United States Patent [19]
Antonini et al.

[11] 3,986,648
[45] Oct. 19, 1976

[54] CAUTERIZING INSTRUMENT AND HOLDER

[76] Inventors: Frank P. Antonini, 3526 DiVisadero, San Francisco, Calif. 94117; Julien I. Schwalbe, 6215 Ascot Drive, Oakland, Calif. 94611

[22] Filed: June 6, 1975

[21] Appl. No.: 584,622

Related U.S. Application Data
[62] Division of Ser. No. 471,197, May 20, 1974, Pat. No. 3,934,715.

[52] U.S. Cl. ............................ 224/5 H; 219/242
[51] Int. Cl.² .......................................... A61N 3/00
[58] Field of Search ............... 15/257; 128/303.13, 128/303.14, 303.15, 303.19; 248/309; 224/2 D, 5 R, 5 A, 5 H, 26 B; 228/57; 219/242; 118/210

[56] References Cited
UNITED STATES PATENTS

| | | | |
|---|---|---|---|
| 1,754,526 | 4/1930 | Rittler | 224/5 A X |
| 3,651,818 | 3/1972 | Vargo | 224/5 R X |
| 3,883,716 | 5/1975 | Fortune | 219/242 |
| D231,031 | 3/1974 | Hinnenkamp | D83/1 F |

FOREIGN PATENTS OR APPLICATIONS 1,278,154  10/1961  France .............................. 248/110

*Primary Examiner*—Edward L. Roberts
*Attorney, Agent, or Firm*—Julian Caplan

[57] ABSTRACT

A disposable cauterizing (electro-surgical) instrument (pencil) is packaged in sterile condition in a sealed envelope. The instrument has a reversible electrode having a narrow needle at one end and a broad flat blade at the other. The handle has an electrical connector consisting of two flat leaves which will accept either end of the electrode and establish electrical contact therewith, the opposite end extending out of the handle in working position. The holder has a sheath which receives the electrode and handle and has a flange which has two slits for attachment of the instrument cord to the holder, a hole to hang, clamp or pin the tab to a drape or other available support and electrode cleaners of two types. One type cleaner is an upstanding boss formed with a V-shaped notch. The other cleaner is a broad tab surface hinged to the flange formed with serrations or abrasive surface.

2 Claims, 8 Drawing Figures

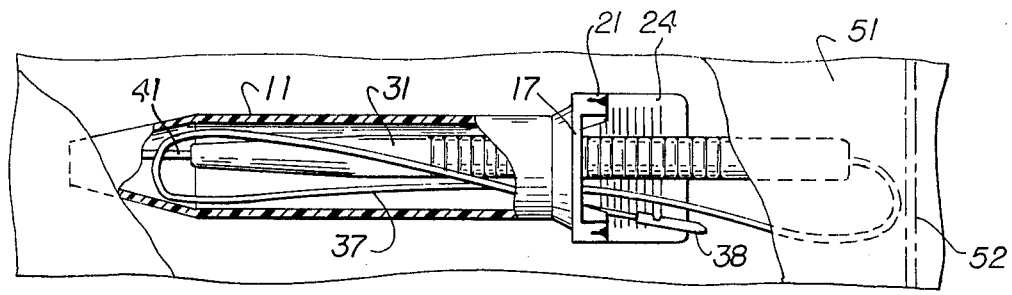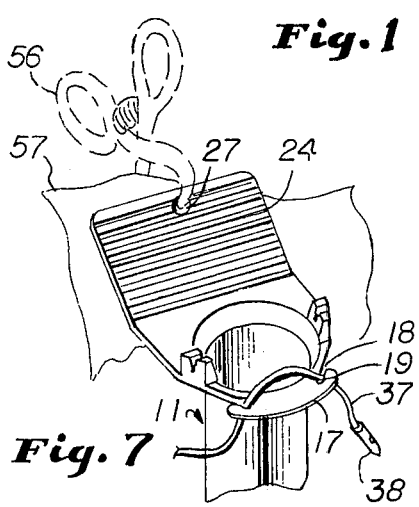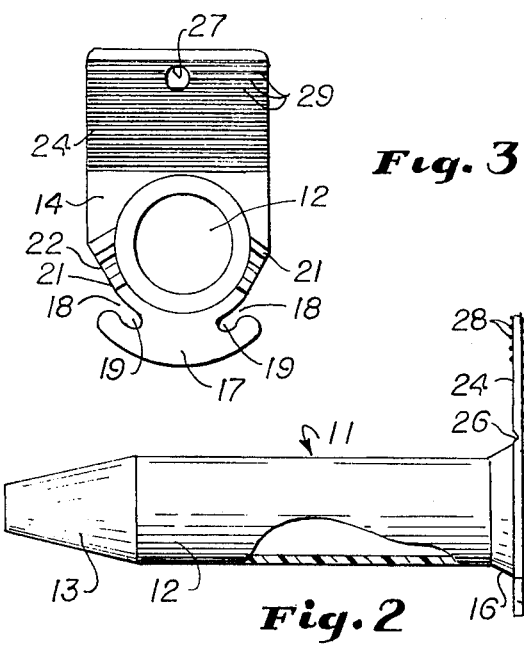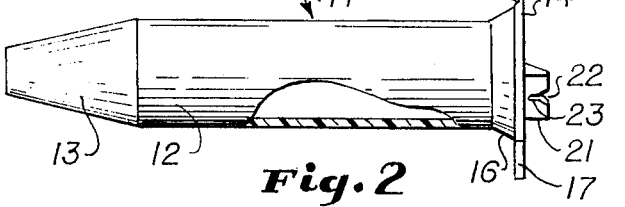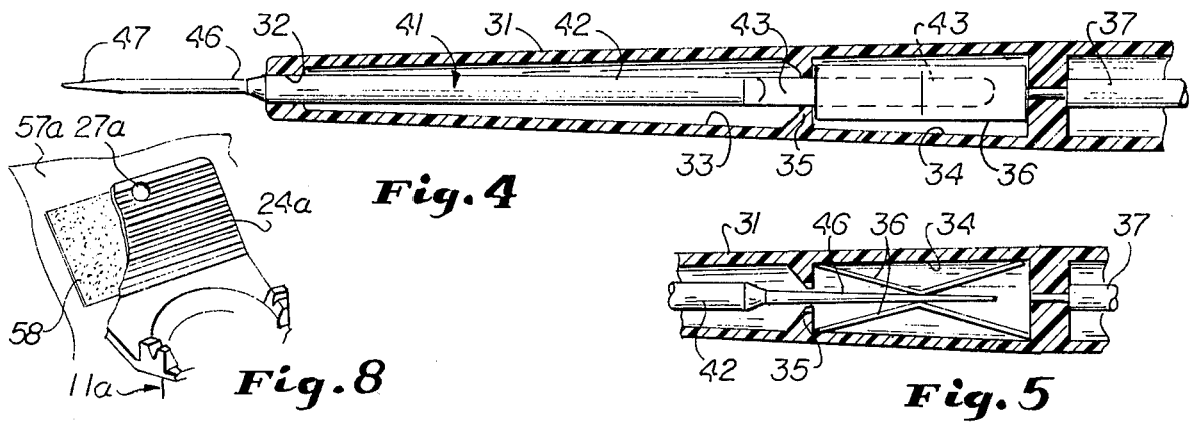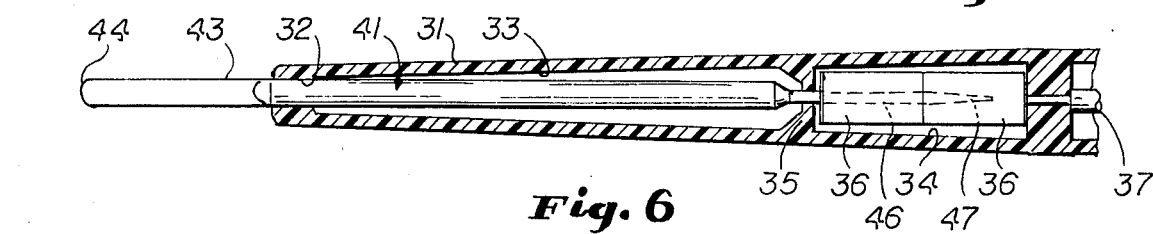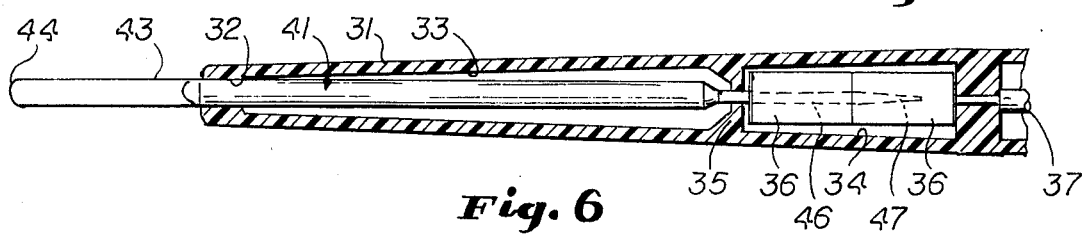

CAUTERIZING INSTRUMENT AND HOLDER

This application is a Divisional Application of Ser. No. 471,197 filed May 20, 1974 now U.S. Pat. No. 3,934,715.

This invention relates to a new and improved cauterizing instrument for electro-surgery and holder therefor.

A feature of the invention is the fact that the instrument consisting of a handle and a electrode insertable in the handle and a holder for the electrode and handle which may be attached to a surgical drape or other support are pre-packaged as a unit in sterile condition and preferably are disposable after use.

A feature of the invention is the fact that the holder is provided with means for attachment to a surgical drape, or other support, and is formed with a sheath which receives the handle and electrode between uses and is shaped so that the instrument may be inserted therein with little attention required by the surgeon. It also has means at its upper end for anchoring the instrument cord to the sheath thus preventing the wire from falling from the sterile field. Further, the upper end of the holder has several means to assist in cleaning the blade during surgery.

A further feature is the fact that the electrode is removable from the handle and has blades of two different shapes at its opposite ends. Thus, either end may be positioned to extend from the handle and the opposite end is received by the handle and holds the electrode assembled. The opposite ends may be a flat blade and a pointed needle for different kinds of surgery or other convenient shapes may be formed.

The interior of the handle has an electrical connector with two electrical contact leaves which are biased to fit tightly against the internal portion of the electrode and establish electrical contact therewith. These leaves are shaped so that they will engage either the flat broad blade or the pointed needle so that either end may be exposed.

Another feature of the invention is the fact that the holder has a tab hinged thereto which is used to attach to a drape or other support with the sheath disposed at any convenient angle. Further, the provision of the hinge makes it possible to fold the tab parallel to the sheath to reduce the bulk of packaging.

Another feature of the invention is the fact that the instrument and its holder are so inexpensive as to be disposable and the entire package may be sold sterile, opened at the time of commencement of the surgery, and then discarded after the surgery.

Other objects of the present invention will become apparent upon reading the following specification and referring to the accompanying drawings in which similar characters of reference represent corresponding parts in each of the several views.

In the drawings:

FIG. 1 is a plan view partly broken away in section to reveal internal construction showing a package for the holder, the instrument and its cord.

FIG. 2 is an enlarged side elevational view partly broken away to reveal internal construction of the holder.

FIG. 3 is an enlarged view of the handle and needle partly broken away to conserve space and to reveal internal construction.

FIG. 5 is a fragmentary view of a portion of the structure of FIG. 4 showing the electrical contacts receiving an end of the needle opposite that received in FIG. 4.

FIG. 6 is a view similar to FIG. 4 showing the needle reversed.

FIG. 7 is a fragmentary view showing the holder clamped to a drape and FIG. 8 shows a modification wherein the holder is attached to a drape by adhesive.

Holder 11 is preferably formed of a plastic material, polypropylene being particularly suitable because of the hinge hereinafter described. Holder 11 has a thin walled sheath 12 which is tapered at the distal end 13 and has an outward flared entrance 16 at the upper end. This shape facilitates dropping the instrument into the sheath when not in use without requiring careful attention by the surgeon. Upward of entrance 16 is a transverse flange 14 formed integral with sheath 12. Flange 14 provides means for attachment of the instrument cord and for cleaning the electrode as hereinafter explained. Lateral extension 17 of flange 14 is arcuate in plan and at either end has inwardly directed slots 18 which terminate in circular enlargements 19. Instrument cord 37 may be slipped into one of the slots 18 in enlargement 19, lain over extension 17, then slipped into the other slot 18 in enlargement 19, to anchor the cord. To either side of the slots 18 are upstanding bosses 21 each formed with a V-shaped slit 22 having a narrow inner extremity 23. The blades of the electrode, hereinafter defined, may be cleaned by drawing the blades through the slits 22.

Opposite extension 17 and hinged to flange 14 by means of hinge 26 is a tab 24. The hinge 26 permits packaging the tab 24 parallel to sheath 12 to reduce bulk (see FIG. 1) and also permits the tab 24 to be bent at a convenient angle relative to sheath 12. Near the outer end of tab 24 is a blind hole 27 into which one side of a drape clamp 56 is fastened to attach the tab to a convenient location on the drape and a plurality of protrusions 28 are formed in a circular pattern around the periphery of the hole 27 on the underside of tab 24 to reduce slippage when the hole 27 is used in this fashion. A plurality of transverse serrations 29 are formed on the top surface of tab 24 and these are also used to clean the blade of the instrument as an alternative to, or as a supplement to, the slits 22.

Handle 41 is formed of a plastic material and has a circular opening 32 at its distal end which is shaped to receive the electrode 41. Immediately inside opening 32 is an electrode receiving recess 33 which is separated from the contact chamber 34 by a partition 35 apertured to receive and guide either end of the electrode. Within chamber 34 is an electrical connector 36 consisting of two brass contact leaves preferably bent as shown in FIG. 5 so that they come together at the middle to grip and establish good electrical contact with either end of the needle. The connector 36 is electrically connected to the inner end of a cord 37 which extends out through the proximal end of handle 31. Cord 37 has a terminal 38 on its remote end to insert into a socket in the electrical portion of the cauterizing machine.

A feature of the invention is the use of a needle 41 which has a round cross-section middle portion 42 and has different shaped blades at opposite ends. End 43 is broad and flat and is beveled to a tapered edge 44. The opposite end of needle 41 has a small diameter portion 46 which terminates in a tapered point 47. The point 47 and the terminus 44, as well as the small diameter end 46 and blade 43, are used in different cauterizing situations. The needle 41 may be withdrawn from the handle 31 and the ends of the needle reversed depending upon the type of blade required. In either position the blade is firmly held in the handle and good electrical contact obtained. Thus the opening 32 is shaped to allow clearance during insertion of either the needle diameter or the blade end. On the other hand, the aperture in partition 35 is non-circular and on one axis has a width equal to the maximum width of broad flat blade 43 and on the opposite axis has a width equal to the diameter of the upper end of needle 46 to guide either needle or blade end into connector 36.

The leaves 36 are bent so that they will engage the broad flat surfaces of end 43 when the needle is in the position shown in FIGS. 4 and 5 and also to engage the small diameter end 46 when the needle is in the position of FIG. 6.

The entire assembly of holder 11, handle 31, electrode 41, cord 37 and terminal 38 is preferably packaged in an envelope 51 of suitable plastic or paper closed at the left end, as viewed in FIG. 1, and formed with a double seal 52 at the right-hand end. The contents are preferably sterilized after packaging. At the time of the operation, the seal 52 is torn open, the flange 14 attached to a surgical drape or other support using a drape clamp 56 or towel clip, and one tooth of the clamp is pressed into blind hole 27 while the opposite tooth of the clamp is pressed to the drape 57 with flange 14 and the drape 57 captured and clamped between the two teeth of the drape clamp 56. The electrode 41 is inserted in the handle 31 with the proper end exposed. As the operation continues, the surgeon occasionally needs to temporarily put down the handle 31 and the holder sheath 12 is used for this purpose. Merely dropping the handle into the sheath protects the handle and electrode 41 from contamination. From time to time if there is an accummulation of material on the electrode, it may be scraped clean either using the slits 22 or the serrations 29. Because of the inexpensive nature of the assembly, the entire assembly may be discarded after use if desired.

In the modification of FIG. 8 a pad 58 having adhesive on opposite faces is attached to the back of tab 24a and is used to attach the holder to drape 57a. Initially the exposed adhesive surface is protected by release paper (not shown), which is peeled off immediately prior to use.

What is claimed is:

1. A holder for an electro-surgical instrument of the type having a handle, an electrode projecting from one end of said handle and a cord extending out the opposite end of said handle, said holder comprising a hollow cylindrical sheath having a closed end and an open end, said sheath shaped to receive said handle and said electrode for easy deposit and withdrawal of said instrument relative to said sheath, and a flange extending transversely of said sheath at said open end, said flange being formed with a substantially rectangular tab hinged thereto extending in a first direction and an extension extending in a second direction opposite said first direction, said tab being formed with means for attachment of said holder to a surgical drape and also with a plurality of transverse serrations for use in cleaning said electrode, said extension being formed with inwardly extending slots on opposite sides into which said cord may be anchored, and a pair of bosses on said flange intermediate said tab and said extension, each said boss having a V-shaped notch for use in cleaning the point of said electrode.

2. A holder according to claim 1 which further comprises adhesive on the back of said tab for attachment of said tab to a surgical drape.

* * * * *